United States Patent
Goldstein

[19]

[11] Patent Number: 6,012,455

[45] Date of Patent: Jan. 11, 2000

[54] NASAL AIR DELIVERY APPARATUS

[76] Inventor: Joseph Goldstein, 1515 Palisades Dr., Suite M, Los Angeles, Calif. 90272

[21] Appl. No.: 09/079,116

[22] Filed: May 14, 1998

Related U.S. Application Data

[63] Continuation-in-part of application No. 08/749,228, Nov. 14, 1996, Pat. No. 5,752,510.

[51] Int. Cl.⁷ ................................................. A61M 15/08
[52] U.S. Cl. ............................... 128/207.18; 128/204.18; 128/206.29
[58] Field of Search ........................ 128/207.18, 200.24, 128/207.14, 200.29, 204.18, 206.29

[56] References Cited

U.S. PATENT DOCUMENTS 5,537,994   7/1996   Thornton ............................ 128/204.18
5,752,510   5/1998   Goldstein ........................... 128/207.18

*Primary Examiner*—John G. Weiss
*Assistant Examiner*—Charles W. Anderson
*Attorney, Agent, or Firm*—Allan M. Shapiro

[57] ABSTRACT

The apparatus is configured to deliver breathable air under continuous positive air pressure to a person who requires such treatment. The apparatus includes a dentally stabilized platform and a nose mask, nose piece or nasal tubes resiliently mounted on the platform and urged toward nasal engagement and rhinal seal. In the case of configurations including nose masks and nose pieces, the force applied from the dentally stabilized platform is through a resilient connection. Various nose masks, nose piece and nostril engaging air tubes carrying nasal pads are disclosed. In each case, the resilient mounting on the dentally stabilized platform provides the necessary air seal. Air which is enhanced by medication or added oxygen may be supplied by the apparatus.

30 Claims, 6 Drawing Sheets

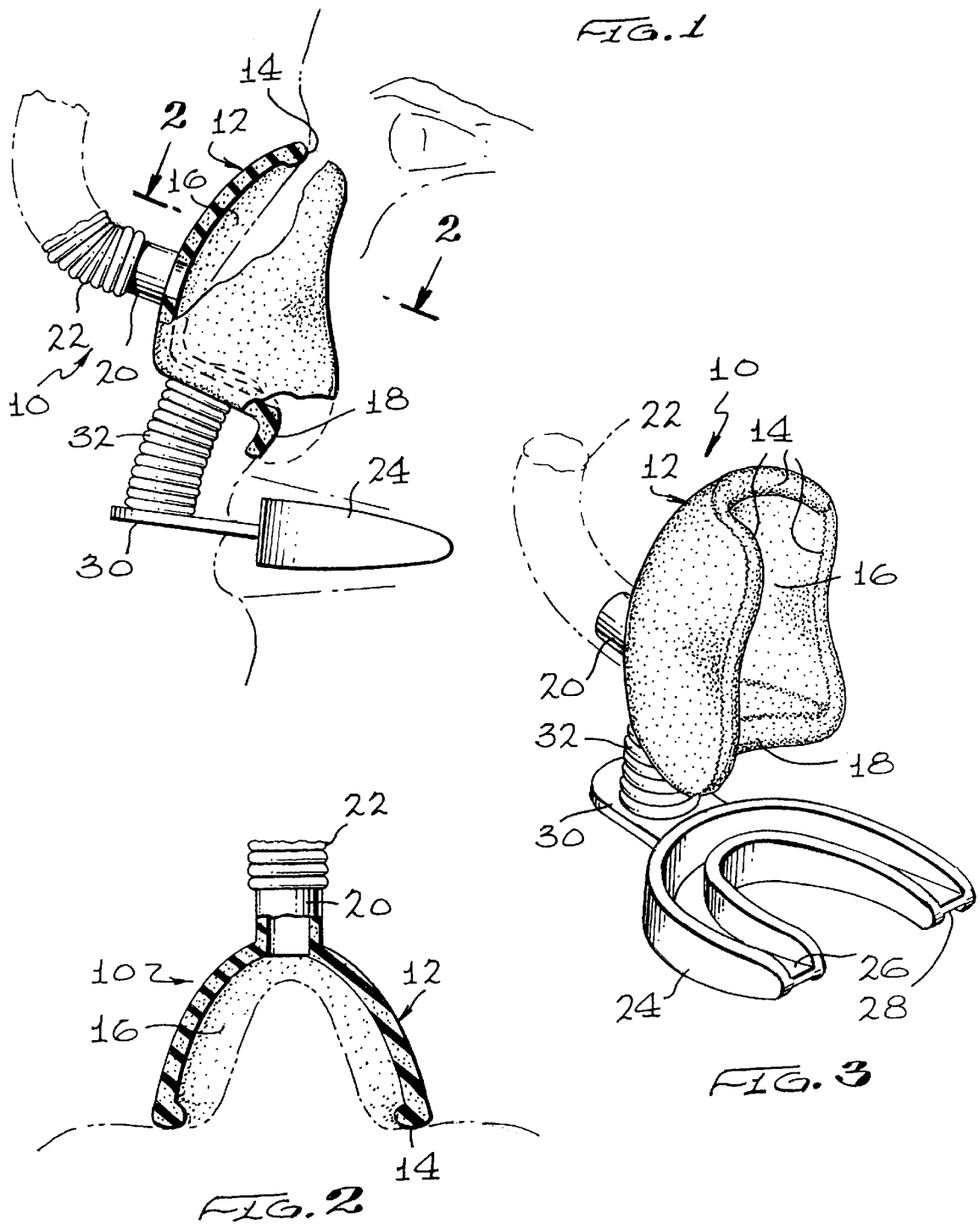

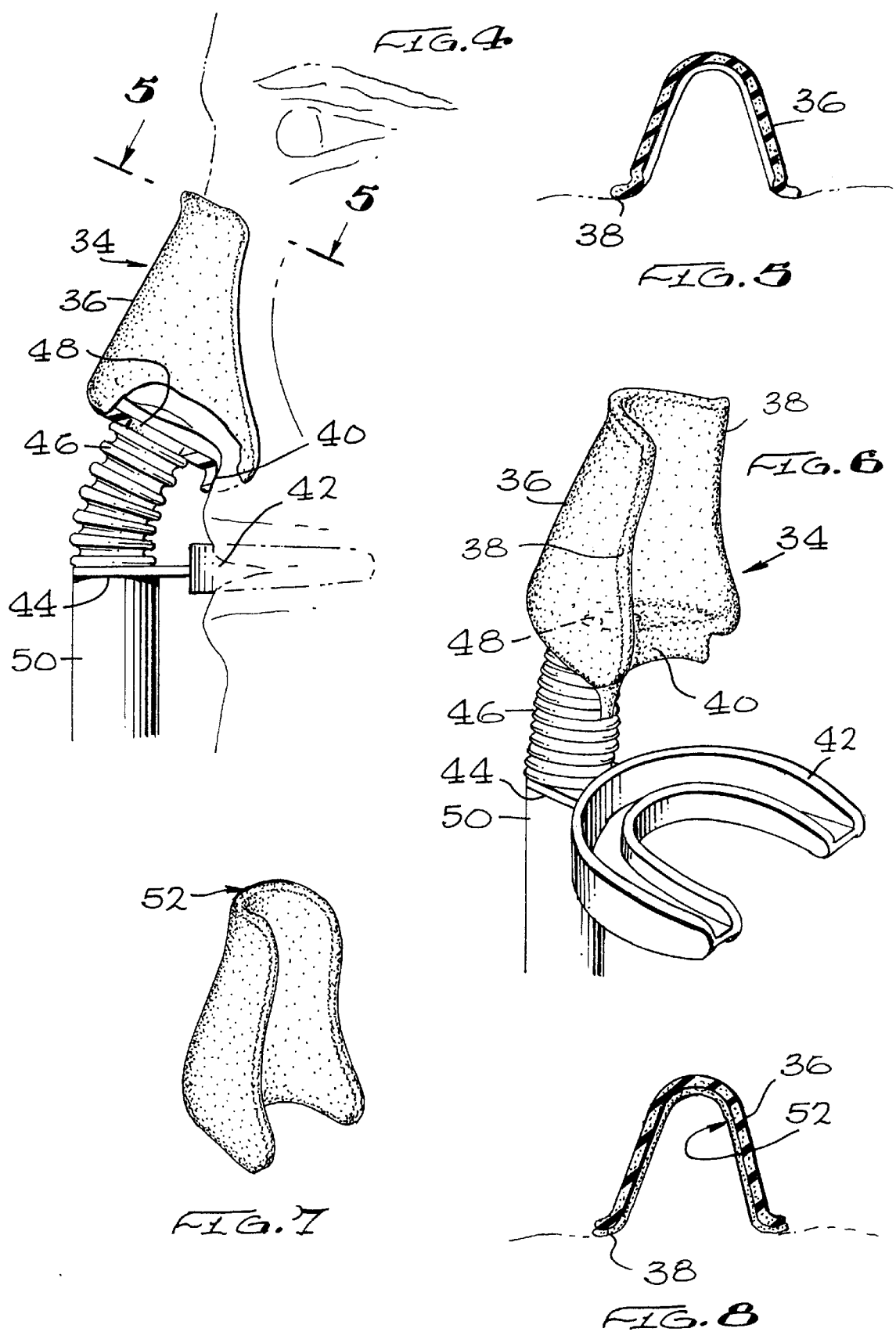

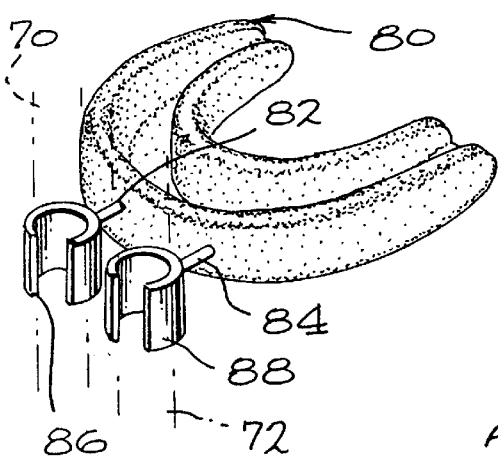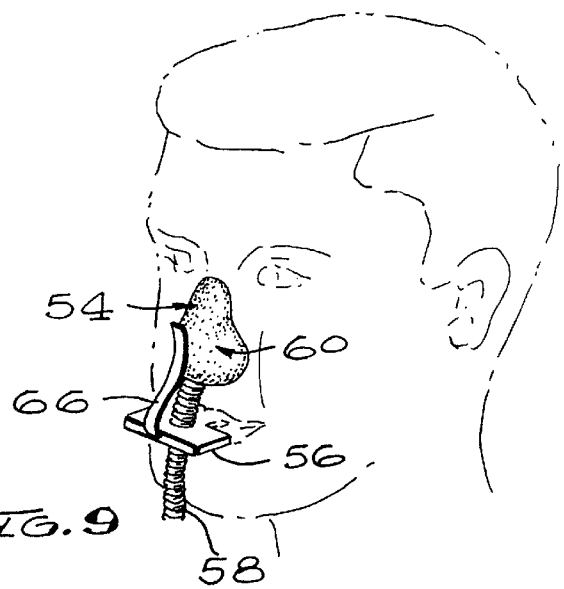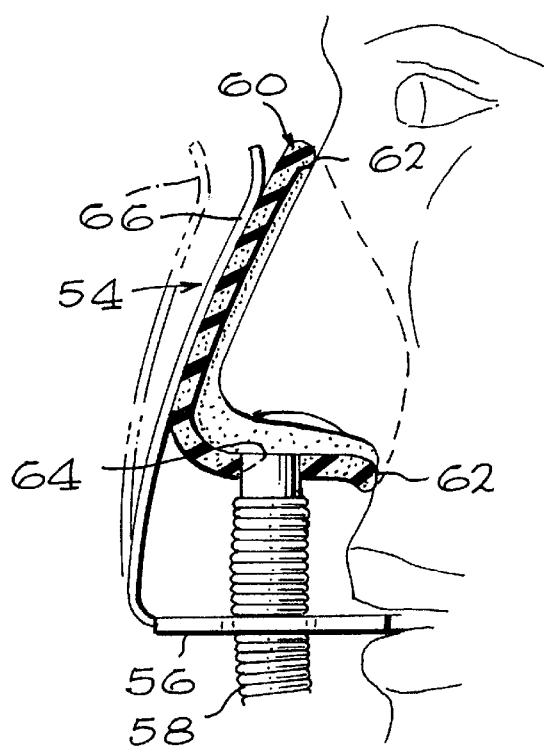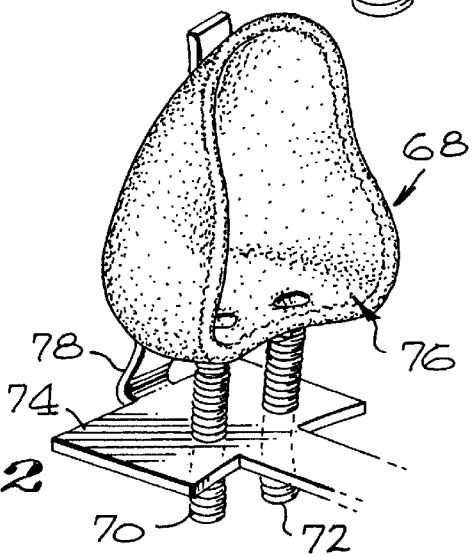

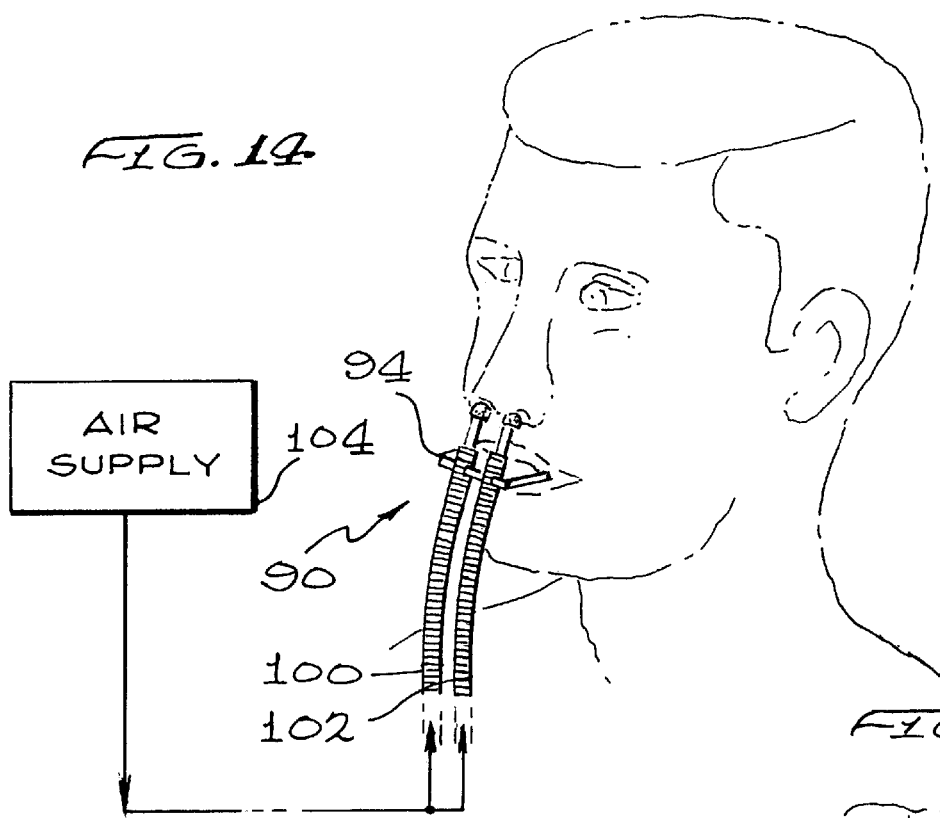
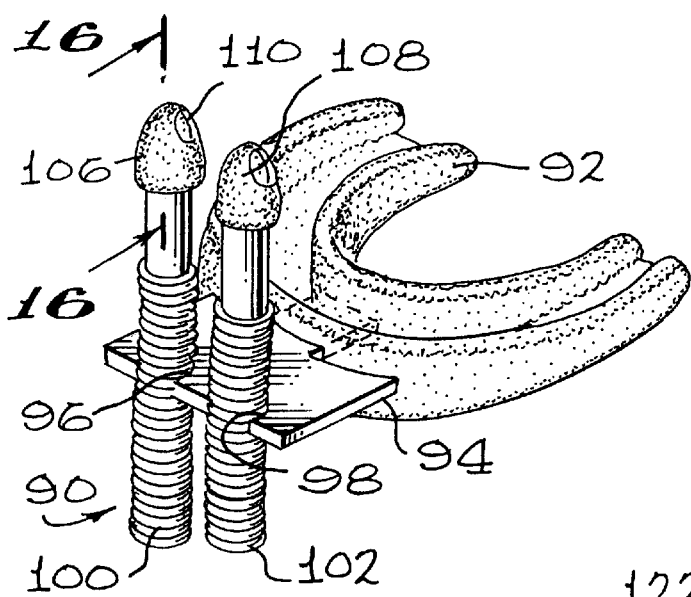
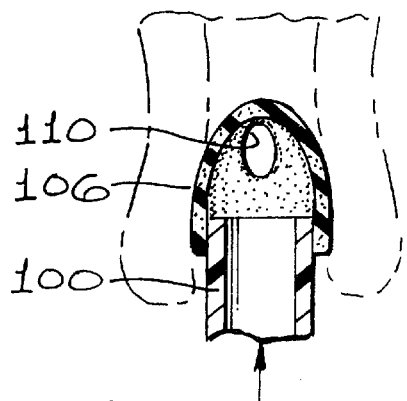
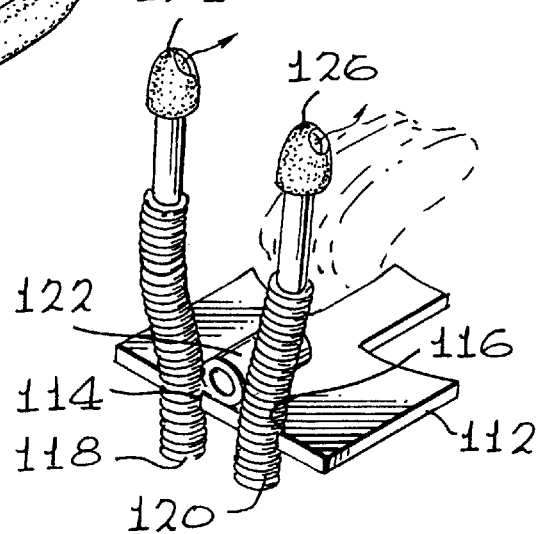

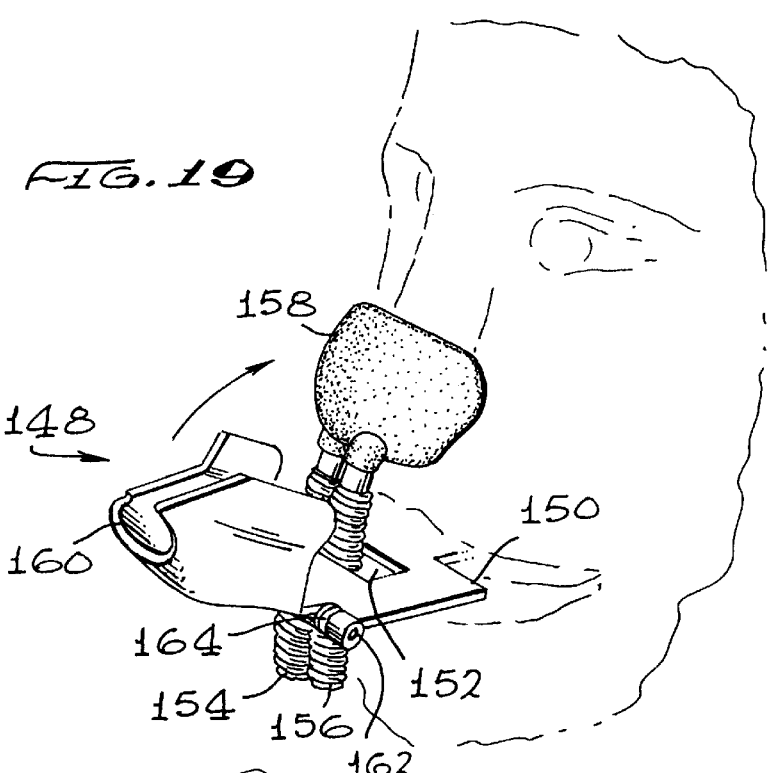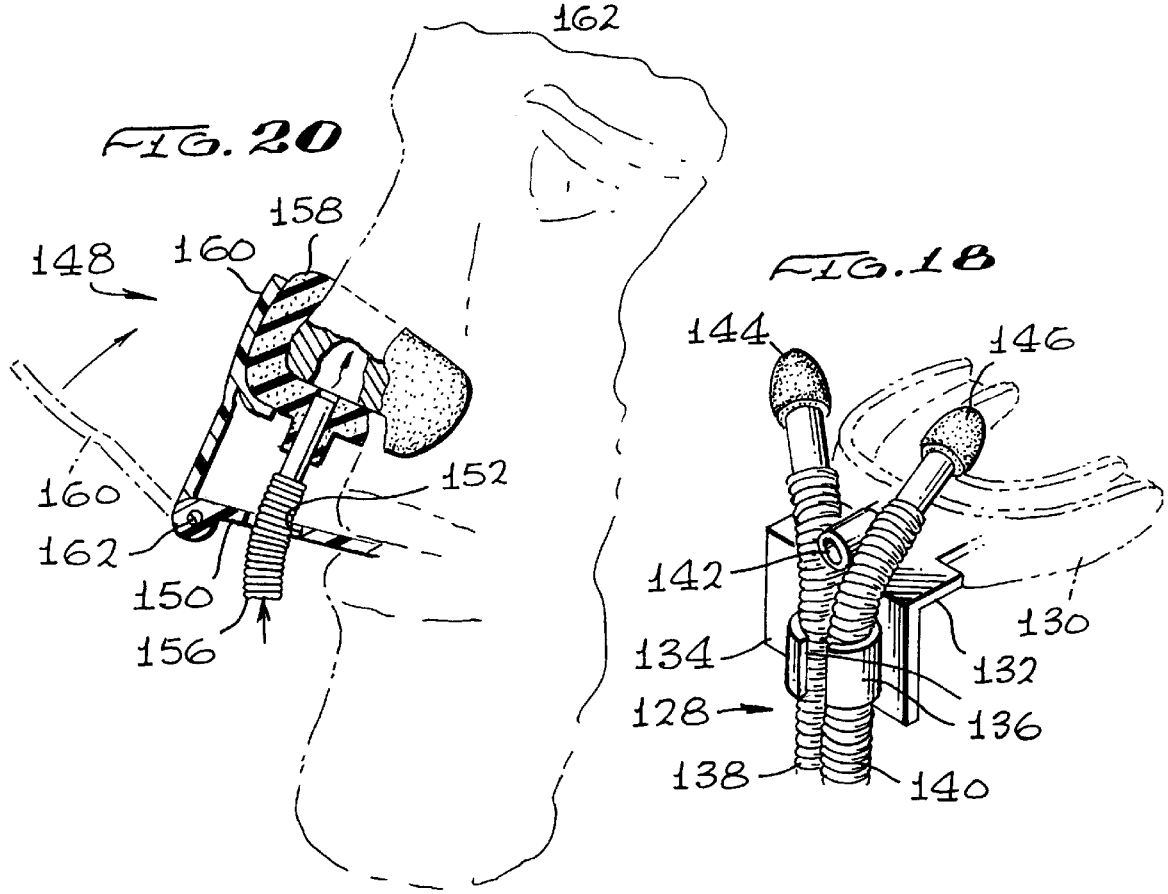

NASAL AIR DELIVERY APPARATUS

CROSS REFERENCE

This application is a continuation-in-part of my earlier patent application Ser. No. 08/749,228, filed Nov. 14, 1996 entitled "Nasal And Oral Air Passageway Delivery Management Apparatus", now U.S. Pat. No. 5,752,510.

FIELD OF THE INVENTION

The present invention is directed to apparatus for directing breathable air to the nasal passages of the patient, particularly while he is sleeping, to alleviate a variety of breathing disorders.

BACKGROUND OF THE INVENTION

In the past, a variety of obstructive sleep disorders or conditions, such as sleep apnea, snoring or the like have been endured by persons. These are generally conditions in which the person's airways, either nasal or oral, become blocked or restricted during sleep. A restricted air supply impairs the flow of oxygen to the person's lungs which, in turn, cuts off the supply of oxygen to the brain. Prior attempts have been made to provide apparatus for alleviating a patient's suffering from such breathing disorders. Modern respiratory therapy provides continuous positive air pressure to the patient so that the positive air pressure acts to keep the airways open. By providing a consistent flow of breathable air at positive pressure to the nasal passages, the adverse affects of sleep apnea and other breathing disorders are often reduced.

Maintaining the apparatus with respect to the user's head is difficult, especially because of the positive pressure aspect. The position of the apparatus must be properly maintained so that the breathable air supply can be reliably delivered to the user's nose. Some apparatus employs an arrangement of straps which engage around the head of the user. Such straps are uncomfortable for sleeping, and are particularly difficult when they are sufficiently tight to hold the apparatus in proper nasal proximity. Most prior devices do not provide a stabilizing or mounting system for adequately supporting the apparatus about the facial area of the user. In addition to support, it is necessary to deliver the stream of breathable air to the nose or adjacent the nostrils. Therefore there is a need to provide an apparatus which can be positioned adjacent the user's nose and sealed with respect to his nose or nostrils so that the supply of breathable air is properly directed and in a reliable relationship with respect to the nose or nasal passages.

SUMMARY OF THE INVENTION

In order to aid in the understanding of this invention it can be said in essentially summary form that it is directed to a nasal air delivery apparatus which is supported by a dentally stabilized platform. An air supply is mounted on the platform and is preferably resiliently urged toward the nose or nasal passages. A nose mask engaging on the face around the nose, a nose piece more closely engaging around the nose or nostril air delivery tubes are contemplated as being supported by the platform.

It is thus a purpose and advantage of this invention to provide a nasal air delivery apparatus which relies upon a dentally stabilized platform and is resiliently urged toward the nose or nasal passages to reliably provide breathable air to the passages, even while the user is sleeping.

It is another purpose and advantage of this invention to provide a nasal air delivery apparatus which relies on a dentally stabilized platform so that it is comfortable and efficient in retaining the nose mask, nose piece or nasal tubes in proper position without the use of straps, head bands or the like.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is a side elevational view of the first preferred embodiment of the air delivery apparatus in accordance with this invention, with parts broken away and parts taken in section.

FIG. 2 is a section of the apparatus as seen generally along line 2—2 of FIG. 1.

FIG. 3 is an isometric view thereof.

FIG. 4 is a side elevational view of a second preferred embodiment of the nasal air delivery apparatus according to this invention.

FIG. 5 is a section taken generally along line 5—5 of FIG. 4.

FIG. 6 is an isometric view of the apparatus of FIG. 4.

FIG. 7 is an isometric view of a liner which can be optionally used within the nose piece shown in FIGS. 4, 5 and 6.

FIG. 8 is a view similar to FIG. 5, showing the appearance of that section when the liner of FIG. 7 is in place.

FIG. 9 is a perspective view of a third preferred embodiment of the nasal air delivery apparatus in accordance with this invention.

FIG. 10 is an isometric view thereof.

FIG. 11 is a substantially centerline section therethrough with parts broken away and parts taken in section.

FIG. 12 is a view similar to FIG. 10, showing the fourth preferred embodiment of the nasal air delivery apparatus in accordance with this invention.

FIG. 13 is a perspective view of a dentally stablized platform in accordance with this invention with collars thereon for detachably retaining air supply tubes for delivery of air to a nose mask, a nose piece or to nasal tubes.

FIG. 14 is a perspective view of a sixth preferred embodiment of the nasal air delivery apparatus in accordance with this invention, showing separate nasal tubes supported on a dentally stabilized platform.

FIG. 15 is an enlarged view thereof.

FIG. 16 is a further enlarged detail taken on line 16—16 in FIG. 15 through one of the nasal tubes with its nasal pad in place.

FIG. 17 is a view similar to FIG. 15, showing a seventh preferred embodiment of the apparatus, wherein the nasal tubes are urged apart.

FIG. 18 is another embodiment of the apparatus, similar to FIG. 17.

FIG. 19 is a ninth embodiment of the nasal air delivery apparatus of this invention, showing a dentally stabilized platform and a nose piece resiliently urged to seal across the nose, with the resilient presser member shown in the retracted position.

FIG. 20 is substantially a center line section of the structure of FIG. 19, but showing the presser member in active position.

DESCRIPTION OF THE PREFERRED EMBODIMENTS

Figure 21:
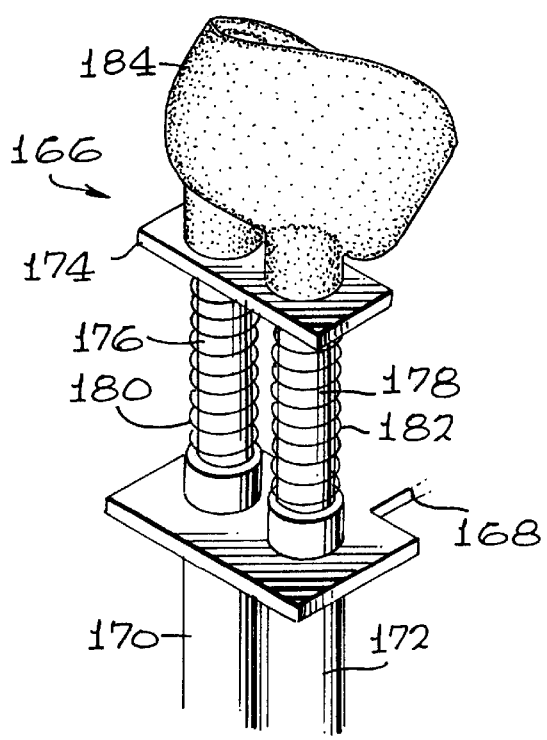
FIG. 21 is an embodiment of the nasal air delivery apparatus of this invention wherein a nose piece is supported on two flexible air delivery tubes and stressed into position.

The first preferred embodiment of the nasal air delivery apparatus of this invention is generally indicated at 10 in FIGS. 1, 2 and 3. The apparatus comprises a nose mask 12 which is configured to be larger than the user's nose so as to enclose the nose without touching. The edge 14 of the nose mask is continuous around the nose so that it can engage on the soft tissues of the face around the nose. The nose mask thus defines cavity 16 around the nose, including around the nostrils. Thus, the nose mask 12 is not a tight fit against the nose, but is sealed at its edges against the face around the nose. The nose mask is preferably made of a fairly stiff but flexible synthetic polymer composition material. It is preferably sufficiently soft so that it can properly seal around the nose on persons of different facial configurations. The edge includes bottom edge 18 which seals against the person's face below his nose and above his upper lip.

Inlet tube 20 is formed as part of the nose mask. Flexible tube 22 can be attached to the inlet tube 20. The flexible tube comes from an air supply device which supplies breathable air as required. This air supply may be a constant supply of breathable air or may be a pulsed supply. Furthermore, the nasal air delivery apparatus 10 may be used for inhalation therapy in which the supply of air may include enhanced oxygen levels or may include medication. As indicated in FIGS. 1 and 3, the flexible tube which supplies the air is preferably led over the top of the head of the user.

In order to retain the nose mask 12 in place, dental anchor 24 is employed. The dental anchor 24 is sized to be engaged between the teeth in the mouth. It preferably has channels 26 and 28 into which the teeth are engaged. The dental anchor may be retained in place simply by jaw strength, with the jaws clamped thereon. On the other hand, the dental anchor can be individually configured to fit the teeth of the user so that the dental anchor actually grips the teeth and jaw strength is thus not required. Platform 30 is attached to dental anchor 24. Platform 30 is preferably thin so that it extends out between the user's lips without significant lip distortion. Platform 30 is thus a dentally stabilized platform. Connector 32 is a resilient connector. In the preferred embodiment shown in FIG. 1, connector 32 is a flexible polymer tube which may have a resilient wire therein so that it can be configured to a neutral position and can be stressed to deflect from the neutral position and provide returning force which urges the nose mask mounted thereon toward the neutral position. Connector 32 does not provide the air connection but provides the resilient force of the nose mask against the soft tissue surrounding the nose.

The nasal air delivery apparatus 34 shown in FIGS. 4 and 6 is a second preferred embodiment. In this embodiment, nose piece 36 is configured to closely fit the nose, particularly see FIG. 5. The nose piece 36 may not exactly fit the nose, as indicated in FIG. 5, but it has a sealing edge 38 which engages the facial tissue closely around the nose. The sealing edge includes a bottom edge which engages the face beneath the nose and above the upper lip. The nose piece 36 is held in place over the nose in a similar manner. A dental anchor 42 is engaged by the teeth to provide a secure attachment point. Platform 44 is secured to the dental anchor and serves as a dentally stabilized platform. It is maintained in position either by jaw strength or by gripping the teeth, depending upon configuration. Platform 44 carries resilient tube 46 thereon. Tube 46 is attached to the bottom of the nose piece and there is an opening 48 in the nose piece to permit communication from the tube to the nose piece. The air supply is upward through supply tube 50. The air supply has the same options as previously described with respect to the air supply tube 22. Resilient tube 46 may be made of flexible polymer composition material and is made in such a manner that it can be configured to a desired position and then resiliently displaced therefrom. For example, nose piece 36 is positioned with respect to the platform 44 so that it forcefully engages against the nose and surrounding tissues of the user. The resiliency of the tube 46 provides the stress when the nose piece is in nose engaging position. The elastic character of the resilient tube may rely upon an embedded metallic or non-metallic spring or it may rely upon the structure of the tube 46 itself.

In order to improve the universality of the fit of the nose piece 36 upon the user's nose, a liner 52 may be employed within the nose piece. As seen in FIG. 7, the liner has an open bottom to avoid closing the air passage at the opening 48 below the nostrils. However, the liner is soft such as low-density synthetic polymer foam so that it can readily accommodate to the nasal shape. In this configuration, the nose piece engages along the bridge and the sides of the nose, as well as below the nose against the upper lip. In this way, the dentally stabilized platform 44 serves as a location from which the nose piece can be supported and resiliently urged against the nose for sealing therearound.

The nasal air delivery apparatus 54 shown in FIGS. 9, 10 and 11 also has a dental anchor in the mouth, not shown, but the same as the previously disclosed dental anchors. Platform 56 is attached to the dental anchor and becomes a dentally stabilized platform. Air supply tube 58 passes through an opening in the platform. Nose mask 60 is mounted on the top of the air supply tube. The nose mask has a sealing edge 62 which is configured to seal around the nose of the user and across the face below the nose and above the upper lip. The nose mask is made of somewhat flexible material, such as a resilient synthetic polymer composition material and is sufficiently flexible to be able to properly seal over a broad range of different facial configurations. Opening 64 in the bottom of the nose mask permits the flow of breathable air, and/or oxygenated or medicated air into the mask for the user. The air supply tube 58 is fairly flexible and in order to maintain the nose mask in sealing engagement around the nose, spring 66 is mounted on the dentally stabilized platform and resiliently engages against the front of the nose mask, urging the nose mask into proper sealing engagement.

FIG. 12 is a perspective view of a nasal air delivery apparatus 68 which is very similar to the apparatus 54. It has the same dental anchor and dentally stabilized platform. In this embodiment two air supply tubes 70 and 72 pass through openings in the dentally stabilized platform 74. The tubes extend above the platform and separately enter the bottom wall of nose mask 76. Spring 78 urges the nose mask, on its flexible air supply tubes 70 and 72 toward engagement with the user to seal around his nose. Resiliently urging the nose mask with respect to the dentally stabilized platform assures proper seal.

FIG. 13 illustrates dental anchor 80 which can be clamped in the jaws of the user. It may be a fitted dental anchor or one which provides an approximate fit. Instead of a flat plate extending out of the front of the dental anchor, two support pins 82 and 84 are secured to the dental anchor and extend out between the user's lips when the dental anchor is in position. First and second collars 86 and 88 are mounted on the support pins. These collars receive and hold a pair of air supply tubes, like the air supply tubes 70 and 72. In such a case, the air supply tubes are resilient and are stressed to press the nose mask mounted on the top of the air supply tubes, like nose mask 76, into sealing engagement with the user around his nose. On the other hand, the air supply tubes grasped by the collars 86 and 88 may be utilized directly as breathable air supply to nose pillows, as shown in FIG. 14.

FIGS. 14 and 15 show a nasal air delivery apparatus 90. It employs a dental anchor 92 from which extends dentally stabilized platform 94. Platform 94 has two notches 96 and 98 therein which receive the air supply tubes 100 and 102. The air supply tubes receive air from a supply source 104 which supplies the proper breathable air at positive pressure. As discussed above, the air supply may be constant or pulsed and it may be employed for inhalation therapy such as by enrichment with oxygen and/or incorporation of medication. The air supply tubes are flexible above the dentally stabilized platform 94. They are flexible so that they can be moved with respect to each other for proper nostril engagement. The upper portions of the air supply tubes are cylindrical tubes and each respectively carries its own nasal pad 106 and 108. The nasal pads are replaceable and resiliently engage over the upper end of the air supply tubes. The nasal pads have openings therein which directed upward and slightly toward the nasal septum. opening 110 is seen in nasal pad 106. The tubes 100 and 102 can be placed at different lengthwise positions with respect to the platform 94 and, in that the way, the engagement distance into the nasal passageway is adjusted. It can be seen how these air supply tubes can be grasped in the same way in the collars 86 and 88 of the structure of FIG. 13.

The dentally stabilized platform 112 shown in FIG. 17 is also mounted in a dental anchor, shown in dashed lines. Platform 12 has notches 114 and 116 therein. These notches are configured the same way as the notches 96 and 98 so that first and second air tubes 118 and 120 can be embraced therein, similarly to the structure in FIG. 15. Spreader 122 is attached to the upper surface of the platform 112 and engages the adjacent sides of the tubes 118 and 120 above the platform. This causes the air supply tubes to divert away from each other in their flexible sections to cause the cylindrical tubular upper outlet portions of the tubes to be stressed away from each other, as seen in FIG. 17. Nasal pads 124 and 126 are engaged on the upper outlet ends of the air tubes. When inserted into the nostrils, the separating force upon the air tubes causes the nasal pads to push outward, away from the nasal septum. In some cases this causes an opening of the nasal air passages to aid in breathing.

The nasal air delivery apparatus 128 shown in FIG. 18 is similar to that shown in FIG. 17. Dental anchor 130, shown in dashed lines, supports dentally stabilized platform 132. The front edge of the platform 132 has a downwardly directed skirt 134 on which is mounted a pair of clamp jaws 136 which clamp around the air supply tubes 138 and 140.

The clamp jaws permit adjustment of the air tubes along their length, within the clamp. Extending from the platform 132 is spreader 142. The spreader 142 lies between the air supply tubes to spread them apart around the spreader 142. This causes the cylindrical upper portions of the air tubes to be laterally divergent. However, the corrugated resilient flexible portion of the air tubes, below the cylindrical upper portions thereof, extend above the spreader so that flexure above the spreader is possible. The cylindrical upper ends of the air tubes are capped with nasal pads 144 and 146, which have air passage openings therethrough, as previously described. The resilient separation of the air tubes at the nasal pads provides a spreading effect when the nasal pads are inserted into the nostrils so that the nasal pads are urged away from the nasal septum, to aid in breathing.

The nasal air delivery apparatus 148 illustrated in FIGS. 19 and 20 comprises a dental anchor, not shown, on which is mounted dentally stabilized platform 150. The platform 150 has a clearance opening 152 therein through which the two air tubes 154 and 156 pass. Nose piece 158 is a soft nose piece which fits around the nostrils and seals around the nose and upper lip close to the nostrils. Air tubes 154 and 156 pass up into nose piece 158 and are in general alignment with the nostrils. Nose piece 158 is made of soft material, such as polymer foam, so that it can readily seal around the nostrils. Cup 160 is of substantially rigid material and is sized to engage around the nose piece 158, see FIG. 20. Cup 160 is pivoted on dentally stabilized plate 150 on pivot pin 162. Spring 164 engages both the plate 150 and the cup and urges the cup in a clockwise direction, as indicated by the arrows in FIGS. 19 and 20. The cup is configured to engage over the nose piece and press it against the nose including upward around the nostrils. In this way, a substantial seal is achieved. The force of the nose piece 158 against the nose is achieved by the spring-loaded cup 160 which acts against the dentally stabilized plate 150.

Nasal air delivery apparatus 166 shown in FIG. 21 has a dentally stabilized plate 168 extending from the mouth of the user. The plate 168 has two air supply tubes 170 and 172 mounted in the plate. Crossbar 174 carries two telescoping air tubes 176 and 178 thereon. There are compression springs 180 and 182 on air tubes 176 and 178, respectively. These springs urge the crossbar upward with respect to the dentally stabilized plate 168. Nose piece 184 is shaped the same as nose piece 158 which is seen in FIGS. 19 and 20. The nose piece 184 is thrust upwardly against the nose with respect to the dentally stabilized plate to achieve a proper seal.

Figure 22:
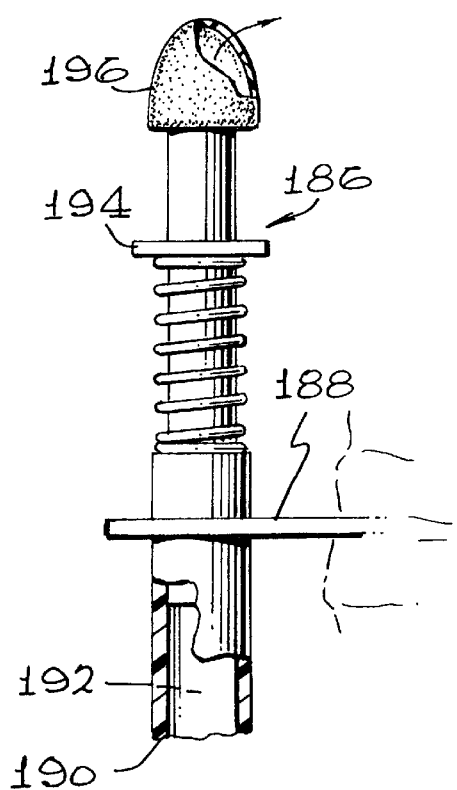
FIG. 22 is a side elevational view of the nasal air delivery apparatus wherein two nasal tubes are mounted on a dentally stabilized platform.

The nasal air delivery apparatus 186 shown in FIG. 22 is similar to the apparatus shown in FIG. 21. There is a dentally stabilized plate 188 which carries first and second air tubes 190 and 192. The cross piece 194 carries the telescoping air tubes and compression springs which thrust the cross piece 194 upward with respect to the dentally stabilized plate. The top outlet ends at these telescoping air tubes carry first and second nasal pads, with the near nasal pad 196 being seen in FIG. 22 and obscuring the other nasal pad immediately beyond it. The springs thrust these nasal pads up into the nostrils to achieve proper seal. The nasal pad outlets are turned to be directed posteriorly and toward the nasal septum.

Figure 23:
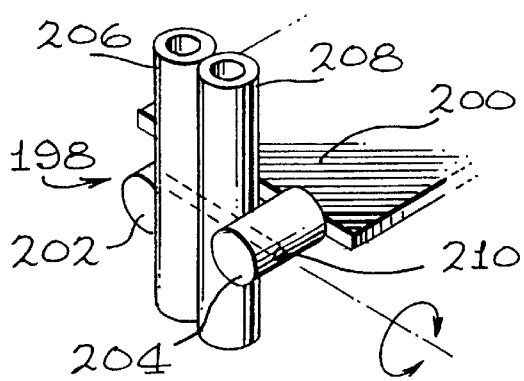
FIG. 23 is another nasal air delivery apparatus wherein the two nasal tubes are pivotally mounted on the dentally stabilized platform.

FIG. 23 illustrates a portion of a nasal air delivery system which is generally indicated at 198. It has a dentally stabilized platform 200 on which is mounted a pair of bosses. The bosses 202 and 204 are shown in FIG. 23. The tubes 206 and 208 are positioned between the bosses and are pivotally mounted thereon on pivot pin 210. These air tubes are the same as the air tubes 170 and 172 or are the same as the air tubes 190 and 192 because they receive a pair of telescoping air tubes which are spring-urged upwardly and carry the nasal pads or the nose piece thereon. Thus, the structure of FIG. 23 is a means for pivotally mounting the air tubes on the dentally stabilized plate and are suitable for different means for direct sealing of telescoping air tubes with respect to the nasal configuration.

Figure 24:
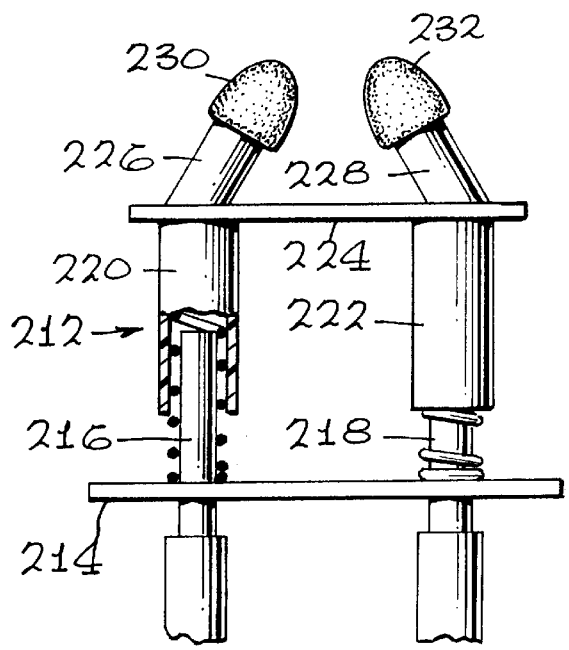
FIG. 24 is a front view, with parts broken away and parts taken in section of the nasal air delivery apparatus wherein the two nasal tubes are resiliently mounted on the dentally stabilized platform.

The nasal air delivery apparatus 212 shown in FIG. 24 has a dentally stabilized platform 214 through which extend and to which are fixed air tubes 216 and 218. Flexible tubes from the breathable air supply are attached to the bottom of these air tubes. The top of these air tubes extend above the dentally stabilized plate and telescoping tubes 220 and 222 slide thereover. Cross piece 224 joins these tubes so that they move together. Springs interengaged in the telescoping structure thrust the cross piece upward with respect to the platform 214. Nasal tubes 216 and 218 are mounted on the top of the cross piece and are in air communication through the cross piece with the telescoping tubes therebelow. The nasal tubes are topped with nasal pads 230 and 232 respectively for engagement in the nasal passages. The nasal tubes 226 and 228 may be directed at an appropriate angle to properly insert the nasal pads and help to spread the nasal passages.

This invention has been described in its presently contemplated best modes and embodiments and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A nasal air delivery apparatus comprising:
    a dental anchor for dental engagement by the patient being treated, a dentally stabilized platform attached to said dental anchor, said dentally stabilized platform being for extending outward from the patient's lips when said dental anchor is dentally engaged by the patient;
    an air source for delivering breathable air to the nose of the patient, said air source for delivering breathable air including a rhinal seal so that substantially all of the breathable air delivered by said air source is delivered to the nasal passages of the patient; and
    a configurable and resilient support connected to said dentally stabilized platform and to said air source for delivering breathable air to shape and thereafter apply force to said air source for delivering breathable air to cause substantial rhinal sealing.

2. The nasal air delivery apparatus of claim 1 wherein said source is a nose mask which seals against the face around the nose.

3. The nasal air delivery apparatus of claim 2 wherein said air source for delivering breathable air includes an air delivery tube connected to said nose mask to deliver breathable air to said nose mask.

4. The nasal air delivery apparatus of claim 3 wherein said air delivery tube is malleable and resilient and is connected to said nose mask in a position so that said air delivery tube can be led over the patient's head when the nasal air delivery apparatus is in use.

5. The nasal air delivery apparatus of claim 3 wherein said malleable and resilient air delivery tube is attached to said dentally stabilized platform.

6. The nasal air delivery apparatus of claim 1 wherein said air source means for delivering breathable air includes a nose mask mounted on said dentally stabilized platform by means of a malleable and resilient tube.

7. The nasal air delivery apparatus of claim 6 wherein said configurable and resilient tube is bent to urge said nose mask into rhinal sealing.

8. The nasal air delivery apparatus of claim 1 wherein said rhinal seal comprises a nose piece which fits closely around the nose.

9. The nasal air delivery apparatus of claim 8 wherein an air tube for supplying breathable air is connected to said nose piece adjacent the patient's nostrils when the apparatus is use.

10. The nasal air delivery apparatus of claim 9 wherein said air tube is attached to said dentally stabilized platform and to said rhinal seal so that air is supplied through said resilient attachment.

11. The nasal air delivery apparatus of claim 10 further including a liner within said nose piece for ensuring sealing of said nose piece with respect to the patient's nose.

12. The nasal air delivery apparatus of claim 1 wherein said air source for delivering breathable air comprises first and second air tubes and first and second nasal pads respectively mounted on said air tubes, said air tubes being attached to said dentally stabilized platform to resiliently urge said nasal pads with respect to said dentally stabilized platform.

13. A nasal air delivery apparatus comprising:
    a dental anchor for dental engagement by the patient to whom nasal air is to be delivered;
    a dentally stabilized platform attached to said dental anchor and positioned for extending out between the patient's lips when said dental anchor is dentally engaged by the patient;
    a nose mask for sealing around the patient's nose;
    an air tube connected to said nose mask to supply breathable air to said nose mask;
    a configurable and resilient spring connected to both said dentally stabilized platform and said nose mask for urging said nose mask into rhinal sealing when said dental anchor is dentally engaged.

14. The nasal air delivery apparatus of claim 13 wherein said nose mask engages around the nose and above the upper lip.

15. The nasal air delivery apparatus of claim 14 wherein said spring connection between said dentally stabilized platform and said nose mask is a configurable tubular spring.

16. The nasal air delivery apparatus of claim 15 wherein said configurable tubular spring is a synthetic polymer tubular spring.

17. The nasal air delivery apparatus of claim 13 wherein said air tube is connected to said nose mask away from said spring along the medial line of said nose mask so that said air tube can be positioned over the head of the patient.

18. A nasal air delivery apparatus comprising:
    a dental anchor for engagement by the patient to whom nasal air is to be delivered;
    a dentally stabilized platform attached to said dental anchor and positioned to extend out of the patient's mouth between his lips when said dental anchor is dentally engaged;
    a nose piece configured to closely fit around at least a portion of the patient's nose adjacent his nostrils to seal said nose piece against the nose, an air opening in said nose piece adjacent the patient's nostrils;
    an air tube for delivering breathable air, said air tube being attached to said dentally stabilized platform and said air tube being attached to said nose piece at said openings in said nose piece to deliver breathable air adjacent the patient's nostrils; and a configurable and resilient support engaging both said dentally stabilized platform and said nose piece for urging said nose piece into rhinal sealing engagement.

19. The nasal air delivery apparatus of claim 18 wherein said configurable and resilient support urging said nose piece into rhinal sealing is said air tube.

20. The nasal air delivery apparatus of claim 19 wherein said air tube is a resilient corrugated air tube having a malleable wire therein.

21. The nasal air delivery apparatus of claim 20 wherein there is a resilient polymer foam cushion within said nose piece to aid in sealing of said nose piece around the patient's nose.

22. The nasal air delivery apparatus of claim 18 wherein there is a resilient polymer foam cushion within said nose piece to aid in sealing of said nose piece around the patient's nose.

23. The nasal air delivery apparatus of claim 18 wherein said resilient means is a spring secured to said dentally stabilized platform, said spring being positioned to engage the exterior of said nose piece and urge said nose piece into sealing engagement with the patient's nose.

24. A nasal air delivery apparatus comprising:
first and second air tubes, first and second nasal pads respectively positioned on said first and second air tubes, said first and second air tubes being configured for insertion into the patient's nostrils, an air supply for supplying breathable air to said first and second air tubes;
a dental anchor for dental engagement by the patient utilizing the nasal air delivery apparatus;
a dentally stabilized platform secured to said dental anchor, said dentally stabilized platform being configured to extend out between the lips of the patient when said dental anchor is engaged in the patient's mouth;
separate stress applying structure engaging both said first and second air tubes and said dentally stabilized platform so that said air tubes and said nasal pads are resiliently held in nostril engaging position.

25. The nasal air delivery apparatus of claim 24 wherein there are means on said platform for engaging said air tubes to urge said nasal pads into nostril engagement.

26. The nasal air delivery apparatus of claim 25 wherein said means on said platform comprises a spreader for spreading said air tubes.

27. The nasal air delivery apparatus of claim 24 wherein there are separate resilient nostril tubes telescopically positioned with respect to said air tubes, said nostril tubes carrying said nasal pads and a spring between said nostril tubes and said air tubes to urge said nostril tubes away from said dentally stabilized platform toward nostril engagement.

28. The nasal air delivery apparatus of claim 27 wherein said nostril tubes are secured together.

29. The nasal air delivery apparatus of claim 24 wherein said stress-applying structure comprises a spreader mounted on said dentally stabilized platform for providing a separating force between said tubes to cause said nasal pads to be stressed away from each other.

30. The nasal air delivery apparatus of claim 24 wherein said separate stress-applying structure comprises springs engaged between said dentally stabilized platform and said nasal pads.

* * * * *